United States Patent
Engler et al.

[19]

[11] Patent Number: 5,979,178
[45] Date of Patent: *Nov. 9, 1999

[54] PROCESS FOR RECOVERING OLEFINS FROM CRACKED GASES

[75] Inventors: Yves Engler, Vincennes, France; Gerard Dupuis, Walnut Creek, Calif.

[73] Assignees: Air Liquide America Corporation, Houston, Tex.; L'air Liquide Societe Anonyme pour L'etude et L'exploitation des procedes Georges Claude, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/991,655

[22] Filed: Dec. 16, 1997

[51] Int. Cl.$^6$ .................................................. F25B 1/00
[52] U.S. Cl. ................ 62/624; 62/908; 62/932; 62/935; 95/55
[58] Field of Search ............................... 62/624, 908, 932, 62/935; 95/55

[56] References Cited

U.S. PATENT DOCUMENTS

| | | | |
|---|---|---|---|
| 4,687,498 | 8/1987 | MacLean et al. | 62/908 |
| 4,761,167 | 8/1988 | Nicholas et al. | 62/908 |
| 5,082,481 | 1/1992 | Barchas et al. | 62/23 |
| 5,085,774 | 2/1992 | Ekiner et al. | 210/500 |
| 5,332,424 | 7/1994 | Rao et al. | 95/47 |
| 5,452,581 | 9/1995 | Dinh et al. | 62/24 |
| 5,634,354 | 6/1997 | Howard et al. | 62/24 |

FOREIGN PATENT DOCUMENTS

| | | |
|---|---|---|
| 0 219 878 | 4/1987 | European Pat. Off. . |
| 0 445 041 | 9/1991 | European Pat. Off. . |
| WO 90/10685 | 9/1990 | WIPO . |

*Primary Examiner*—Ronald Capossela
*Attorney, Agent, or Firm*—Burns, Doane, Swecker & Mathis L.L.P.

[57] ABSTRACT

A process for recovering olefins from a cracking effluent containing olefins and hydrogen. The process comprises compressing the cracking effluent in at least one compression stage to form a compressed cracking effluent, contacting the compressed cracking effluent with a membrane at conditions effective to obtain a permeate stream rich in hydrogen and a retentate stream depleted in hydrogen, and introducing the permeate stream into a pressure swing adsorption system at conditions effective to obtain a non-adsorbed stream rich in hydrogen and a desorbed stream comprising olefins.

14 Claims, 5 Drawing Sheets

PROCESS FOR RECOVERING OLEFINS FROM CRACKED GASES

FIELD OF THE INVENTION

This invention generally relates to the separation of olefins from cracked gases. More particularly, the invention relates to an improved process for separating olefins from cracked gases by removing hydrogen therefrom using a combination of membrane and pressure swing adsorption techniques.

BACKGROUND OF THE INVENTION

Olefins such as ethylene, propylene, and butylene may be produced by heating saturated hydrocarbons such as ethane, propane, or butane at elevated temperatures. Likewise, naphtha, gas oil, and other heavy hydrocarbon feeds may be thermally cracked in a cracking furnace in the presence of steam to produce olefins.

The cracking effluent produced by heating a saturated hydrocarbon, naphtha, or gas oil feed typically contains hydrogen, steam, carbon dioxide, carbon monoxide, methane, ethane, ethylene, propane, propylene, and minor amounts of other components such as heavy hydrocarbons. The cracking effluent is then sent to a product recovery section of the olefins plant.

In the product recovery section, the cracking effluent is compressed in one or more compression stages to partially liquefy the hydrocarbon components for separation via cryogenic distillation. Carbon dioxide, steam, and heavy hydrocarbons must be removed prior to chilling the cracking effluent to prevent them from freezing and plugging the equipment. After removal of these components from the cracking effluent, the effluent is passed to a cryogenic section (commonly referred to as a "Cold Box") where the temperature of the effluent is reduced such that separation of the hydrocarbon components can be performed by distillation. The refrigeration balance of the Cold Box is provided by an ethylene refrigeration cycle for the warmer part of the Cold Box and by expanders of off-gas streams for the colder part of the Cold Box.

The distillation section typically contains three columns, a demethanizer which removes the light ends, a deethanizer which removes the heavy ends, and an ethane/ethylene splitter which separates the ethylene product from the ethane recycle stream. The reboil and condensing duties of the distillation section are also provided by the ethylene refrigeration cycle.

Hydrogen contained in the cracked gases is used, in part, for balancing the cold end of the cryogenic section. However, its presence requires colder temperatures in the distillation section to separate the products. Hydrogen also acts as a ballast in the distillation section, which prevents additional quantities of products from being processed.

In view of the drawbacks associated with the presence of hydrogen in the cracking effluent, various methods have been proposed to remove hydrogen from the cracking effluent. See, e.g., U.S. Pat. Nos. 5,082,481, 5,452,581, and 5,634,354; the contents of which are hereby incorporated by reference. The methods described in these patents include the use of a membrane separator to remove hydrogen from the cracking effluent.

However, there are several drawbacks associated with these methods. For example, unless the disclosed methods employ very selective membranes, varying amounts of products are lost in the permeate stream. Even when using highly selective membranes, the hydrogen rejection rate may not be sufficiently high to make the process commercially viable.

Accordingly, there is a need in the art for a process that minmizes or eliminates product losses in the permeate stream without the need to use very selective membranes. In addition, there is a need in the art for a process that can employ higher hydrogen rejection rates without the concomitant loss of product.

SUMMARY OF THE INVENTION

The present invention addresses the aforementioned need in the art by providing an improved process for recovering olefins from a cracking effluent containing olefins and hydrogen. The process comprises compressing the cracking effluent in at least one compression stage to form a compressed cracking effluent, contacting the compressed cracking effluent with a membrane at conditions effective to obtain a permeate stream rich in hydrogen and a retentate stream depleted in hydrogen, and introducing the permeate stream into a pressure swing adsorption system at conditions effective to obtain a nonadsorbed stream rich in hydrogen and a desorbed stream comprising olefins.

In a preferred embodiment, the invention relates to a process for recovering olefins and high purity hydrogen from a cracking effluent. The process comprises compressing the cracking effluent in at least one compression stage to form a compressed cracking effluent, contacting the compressed cracking effluent with a membrane at conditions effective to obtain a permeate stream rich in hydrogen and a retentate stream depleted in hydrogen, compressing the permeate stream in at least one additional compression stage to form a compressed permeate stream, introducing the compressed permeate stream into a pressure swing adsorption system at conditions effective to obtain a nonadsorbed stream comprising high purity hydrogen and a desorbed stream comprising olefins, and recycling the desorbed stream to the at least one compression stage.

DETAILED DESCRIPTION OF THE PREFERRED EMBODIMENTS

Figure 1:
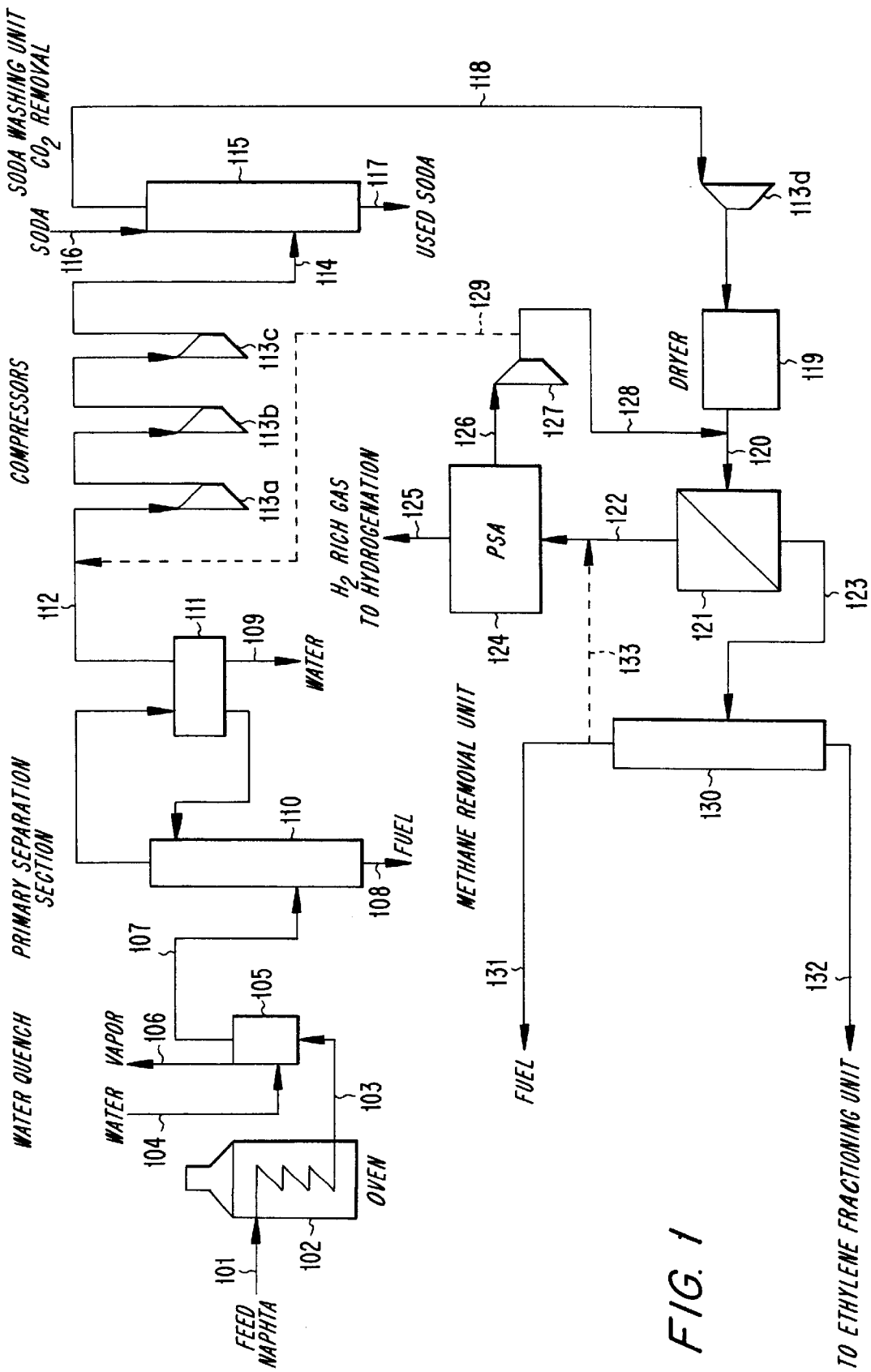
FIG. 1 is a schematic flow diagram of one embodiment of the present invention.

In the present invention, a membrane separator and a pressure swing adsorption (PSA) system are advantageously used in combination. In particular, the permeate stream from the membrane separator, which contains predominantly hydrogen and some valuable products such as olefins, is optionally recompressed in one or more compressors and fed into a PSA system. The PSA system preferentially adsorbs the products present in the permeate stream to yield a nonadsorbed stream rich in hydrogen. The adsorbed products are desorbed at low pressure to yield a desorbed stream comprising the products. The desorbed stream may be recycled to the suction side of at least one of the compression stages. Alternatively, the desorbed stream may be compressed in one or more additional compressors and recycled to the feed side of the membrane separator.

Any membrane may be used in the process of the present invention so long as it is substantially permeable to hydrogen and substantially impermeable to hydrocarbons such as ethylene. Additionally, the membrane should have good compatibility with the gases to be separated, strong structural strength to endure high transmembrane pressure differentials, an adequate flux for given separation parameters, and the like. Such membranes may be made of polymeric materials such as cellulosic derivatives, polysulfones, polyamides, polyaramides, and polyimides. Such membranes may also be made of ceramic, glass, and metal. Preferred membranes for use in the present invention include those described in EP 219,878 and U.S. Pat. No. 5,085,774; the contents of which are hereby incorporated by reference.

The membrane employed in the present invention may be contained in one or more membrane stages, which may be in the form a membrane separator. A membrane separator may contain a series of alternating layers of membranes and spacers which are wrapped around a collection pipe in a "spiral wound" fashion. Gas enters the separator, and the permeate will pass through the wrapped membranes and into the collection pipe. The permeate passes through the collection pipe and exits the separator through an outlet. Non-permeating gases, i.e., retentate or residue, exit the separator through another outlet.

In another alternative, the membrane may be in the form of hollow fibers. In such a separator, gas which enters the separator contacts the fiber membrane. The permeate enters the hollow fibers while the non-permeating gases, i.e., retentate or residue, remain outside the fibers. The permeate travels at reduced pressure inside the fibers to a manifold which conducts the permeate to a permeate outlet. The retentate travels to a separator outlet at essentially the same pressure as the entering feed gas.

Examples of the above-mentioned membrane separators are further described in Spillman, "Economics of Gas Separation Membranes," *Chemical Engineering Progress*, January 1989, pp. 41–62; Haggin, "New Generation of Membranes Developed for Industrial Separations," *Chemical and Engineering News*, Jun. 6, 1988, pp. 7–16; and "MEDAL-Membrane Separation System, Du Pont/Air Liquide."

Suitable PSA systems for use in the process of the present invention are well known in the art and are available from industrial gas companies in the United States. Briefly, a PSA system employs one or more adsorbent beds to selectively adsorb and desorb gas component(s) from a gas mixture through a combination of pressure cycles and valve sequencing.

As advantageously employed in the present invention, the PSA system can produce a high purity hydrogen product which is substantially free of the more strongly adsorbed hydrocarbons and contains at least 98% by volume of hydrogen. The PSA system also can yield a desorbed stream comprising methane, ethane, ethylene, and higher hydrocarbons as well as some hydrogen typically lost in depressurization and purge steps.

By using a combination of membrane and PSA separation systems in accordance with the present invention, it is possible to employ a less selective membrane and/or a higher hydrogen rejection rate without losing valuable products in the permeate stream as in prior art processes. In the present invention, the valuable products are captured in the PSA system and are optionally recycled and recovered. By operating at a higher hydrogen rejection rate, the capacity of the distillation section to separate products can be increased and the cryogenic section can be run at warmer temperatures. Additionally, the process of the present invention allows larger quantities of pure hydrogen to be recovered in the PSA system, resulting in better overall plant economics.

Various preferred embodiments of the present invention will now be described with reference to the drawings wherein like referenced parts have like numerals.

Referring to FIG. 1, a naphtha feed 101 is introduced into a cracking furnace 102. The naphtha feed 101 is thermally cracked in the presence of steam in the cracking furnace 102 to yield a cracking effluent 103. The cracking effluent 103 generally contains hydrogen, steam, carbon monoxide, carbon dioxide, and a range of hydrocarbon products including ethylene, propylene, and other olefins. The cracking effluent 103 is quenched with water 104 in a quencher unit 105. Water vapor is discharged from the quencher unit 105 in line 106. A quenched cracking effluent 107 is withdrawn from the quencher unit 105 and passed to a primary separation section to remove heavy fractions 108 and to knock out steam condensate 109. The primary separation section comprises a distillation column 110 and a condenser 111. Product vapors 112 are withdrawn from the condenser 111 and passed to a series of compressors 113a, 113b, 113c, and 113d wherein the product vapors 112 are compressed to a pressure suitable for subsequent cryogenic olefins recovery. Prior to the final compression stage 113d, the compressed stream 114 is treated in a scrubber 115 with soda 116 to remove $CO_2$. Used soda 117 is withdrawn from the scrubber 115. The scrubbed gas 118 from the scrubber 115 is then passed to the final compressor 113d and introduced into a dryer 119 to remove residual water therefrom. A preconditioned cracking effluent 120 is withdrawn from the dryer 119.

The preconditioned cracking effluent 120 is passed to a membrane separator 121 at conditions effective to obtain a permeate stream 122 rich in hydrogen and a retentate stream 123 depleted in hydrogen. The permeate stream 122 is compressed in one or more additional compressors (not shown), if necessary, and then introduced into a PSA system 124 at conditions effective to produce a nonadsorbed stream 125 rich in hydrogen and a desorbed stream 126 comprising hydrocarbon products from the permeate stream 122. The desorbed stream 126 is compressed in compressor 127 and recycled to the feed side of the membrane separator 121 in line 128. Optionally, as shown by dotted line 129, at least a portion of the compressed desorbed stream 128 is recycled to the suction side of compressor 113a.

The retentate stream 123 comprising hydrocarbons and depleted in hydrogen is separated into its various components in a cryogenic separation section (not shown). The cryogenic section comprises a demethanizer 130 which separates methane 131 from the heavier hydrocarbon products 132. The heavier hydrocarbon products 132, which comprises ethylene, are then passed to additional fractionation columns (not shown) to yield streams of desired product. Optionally, as shown by dotted line 133, at least a portion of the methane overhead stream 131 is recycled to the PSA system 124.

Figure 2:
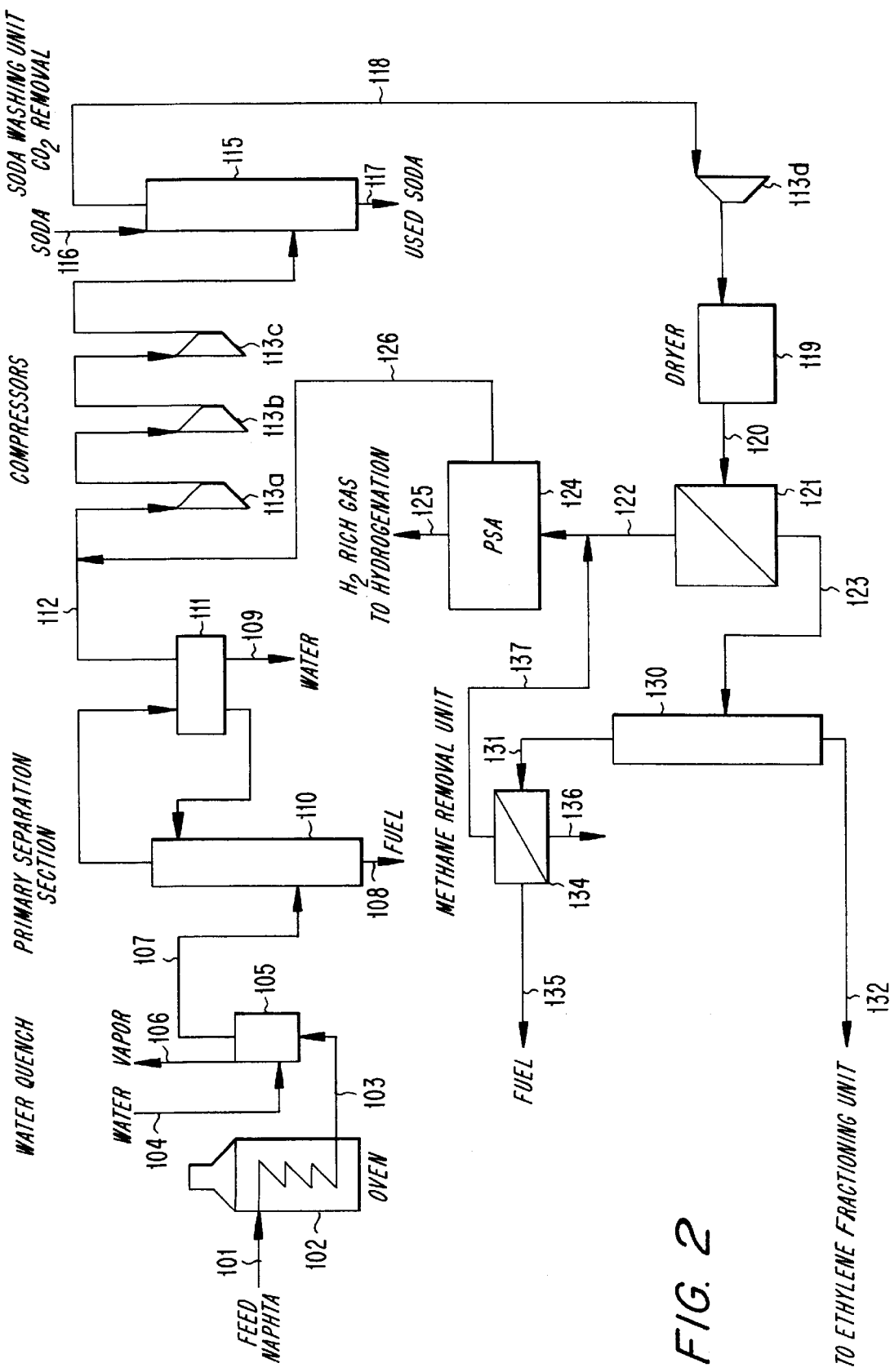
FIG. 2 is a schematic flow diagram of another embodiment of the present invention.

Referring to FIG. 2, the process depicted therein is the same as that depicted in FIG. 1 up to the PSA system 124. In the process of FIG. 2, the desorbed stream 126 which comprises hydrocarbon products is simply recycled back to the suction side of compressor 113a. Additionally, a membrane separator 134 is employed to separate hydrogen from off-gas 135 in the overhead stream 131 of the demethanizer 130. The membrane separator 134 can employ the same or different membrane from that in membrane separator 121. The membrane separator 134 is run at conditions effective to produce a permeate stream 135 rich in hydrogen and a retentate stream 136 depleted in hydrogen. As shown in line 137, at least a portion of the permeate from the membrane separator 134 is recycled to the PSA system 124.

The present invention will now be described with reference to the following examples.

hydrocarbons. As noted above, a portion 6 of the overhead stream 4 is used to provide refrigeration duty to the expanders. The remaining portion 7 of the overhead stream 4 is passed to the PSA system which yields a nonadsorbed stream 8 comprising high purity hydrogen and a desorbed tail gas stream 9. The distillation feedstream 5 is passed to the distillation section to yield an ethylene product stream.

Figure 3:
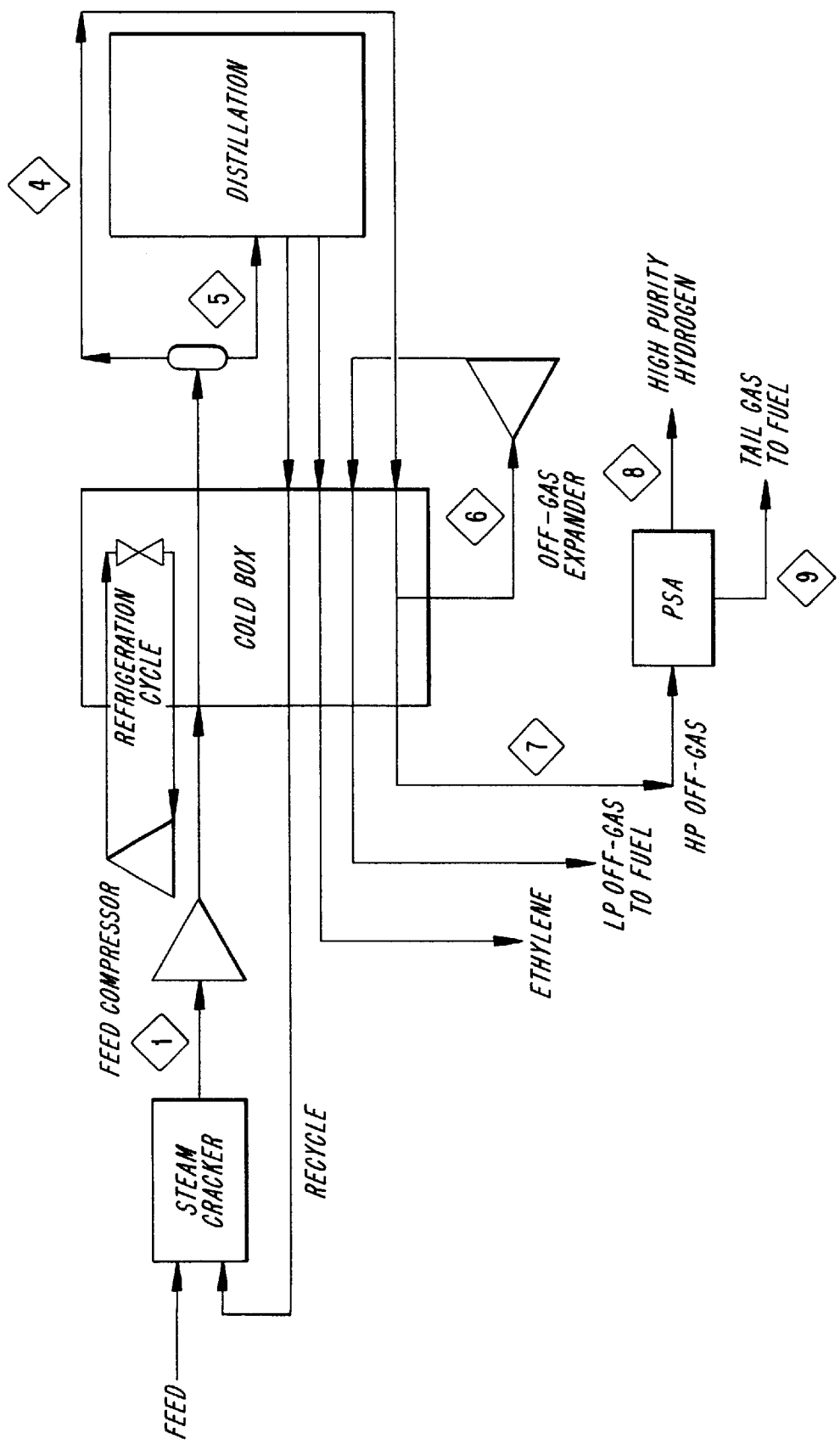
FIG. 3 is a schematic flow diagram of a typical ethylene plant using PSA.

The simulated results of the process scheme depicted in FIG. 3 are summarized in Table 1 below.

Table 1

| Membrane Recovery | N.A. |
| L/V | 70% |
| PSA Recovery | 87% |
| $C_2/C_2=$ Loss | 1.5% |

| Stream No. | Cracker Outlet 1 | Gas from Separator 4 | Expander Feed 6 | PSA Feed 7 | $H_2$ from PSA 8 | PSA Tail Gas 9 | To Distillation 5 |
| --- | --- | --- | --- | --- | --- | --- | --- |
| $H_2$ | 2500.0 | 2400.0 | 480.0 | 1920.0 | 1670.4 | 249.6 | 100.0 |
| $C_1$ | 2000.0 | 540.0 | 108.0 | 432.0 | 0.0 | 432.0 | 1460.0 |
| $C_2=$ | 2700.0 | 48.0 | 9.6 | 38.4 | 0.0 | 38.4 | 2652.0 |
| $C_2$ | 1300.0 | 12.0 | 2.4 | 9.6 | 0.0 | 9.6 | 1288.0 |
| $C_3=$ | 1100.0 | 0.0 | 0.0 | 0.0 | 0.0 | 0.0 | 1100.0 |
| $C_3$ | 400.0 | 0.0 | 0.0 | 0.0 | 0.0 | 0.0 | 400.0 |
| | | | | | | | |
| Total | 10000.0 | 3000.0 | 600.0 | 2400.0 | 1670.4 | 729.6 | 7000.0 |
| $H_2$ (%) | 25.0 | 80.0 | 80.0 | 80.0 | 100.0 | 34.2 | 1.4 |
| $C_1$ (%) | 20.0 | 18.0 | 18.0 | 18.0 | 0.0 | 59.2 | 20.9 |
| $C_2=$ (%) | 27.0 | 1.6 | 1.6 | 1.6 | 0.0 | 5.3 | 37.9 |
| $C_2$ (%) | 13.0 | 0.4 | 0.4 | 0.4 | 0.0 | 1.3 | 18.4 |
| $C_3=$ (%) | 11.0 | 0.0 | 0.0 | 0.0 | 0.0 | 0.0 | 16 |
| $C_3$ (%) | 4.0 | 0.0 | 0.0 | 0.0 | 0.0 | 0.0 | 5.7 |
| | | | | | | | |
| Total (%) | 100.0 | 100.0 | 100.0 | 100.0 | 100.0 | 100.0 | 100.0 |

EXAMPLES

Figure 4:
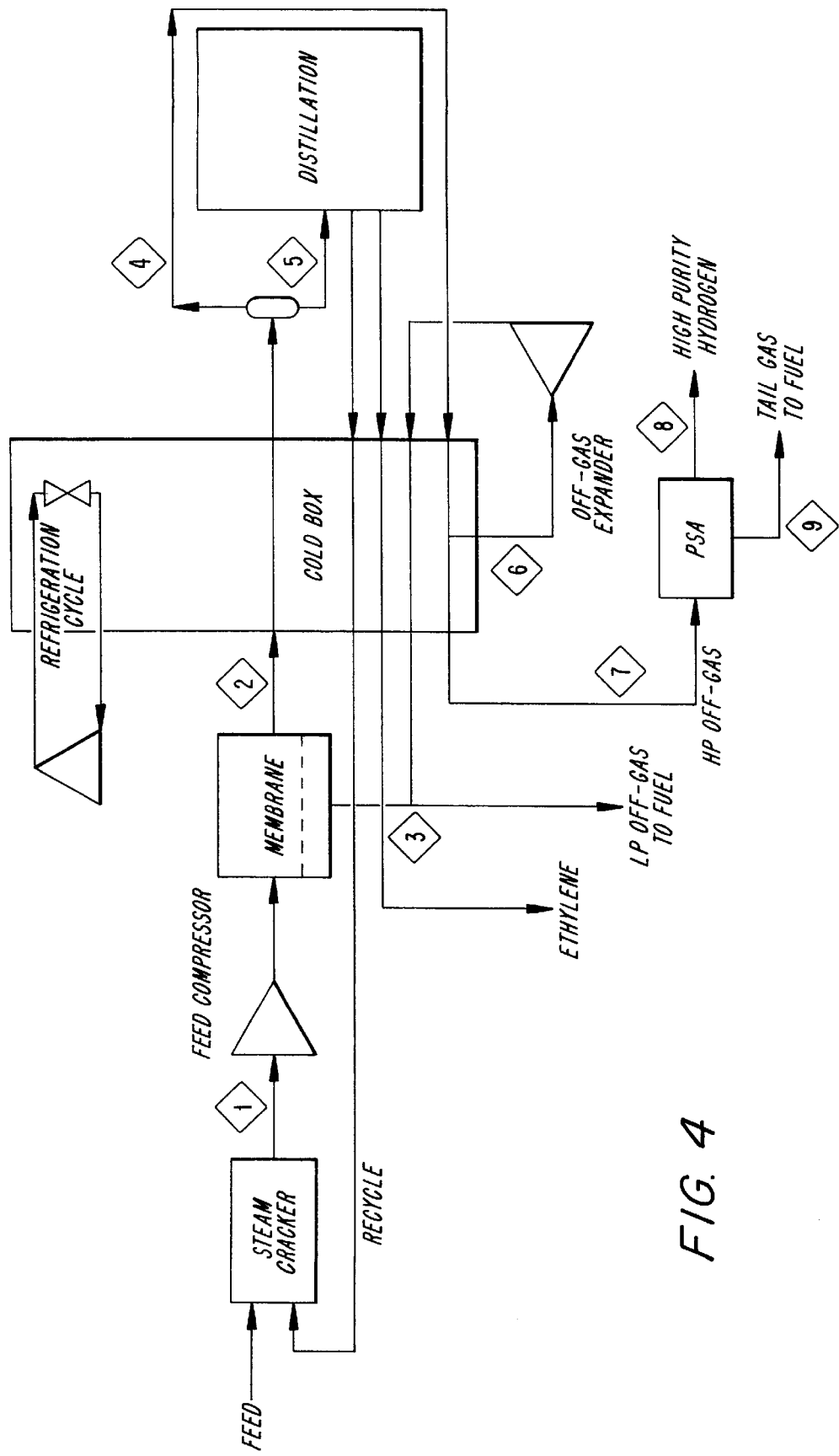
FIG. 4 is a schematic flow diagram of a typical ethylene plant using separate PSA and membrane systems.
Figure 5:
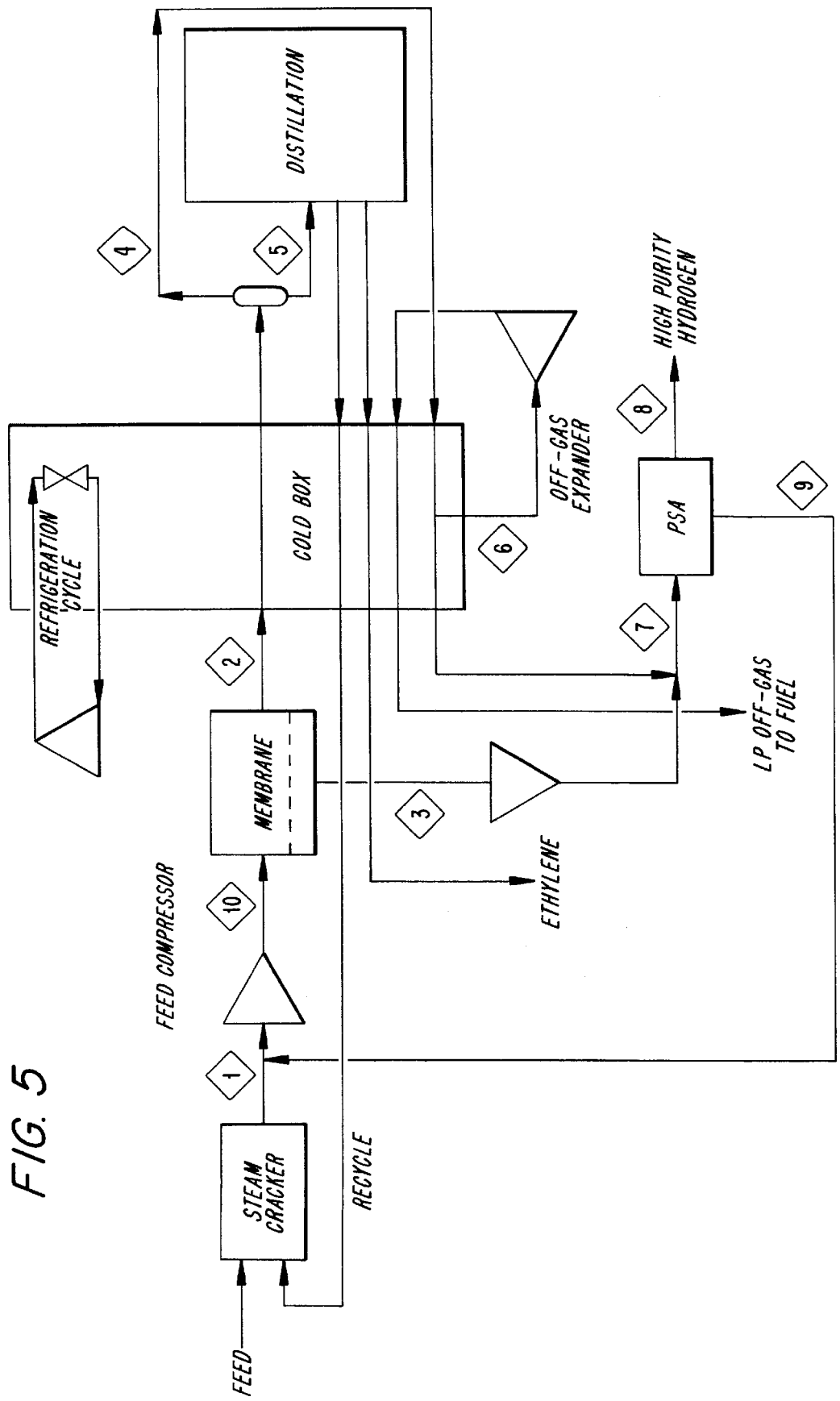
FIG. 5 is a schematic flow diagram of an ethylene plant in accordance with the present invention.

Computer simulations were run based on the process schemes depicted in FIGS. 3–5. The ethylene plants depicted therein were simulated to operate at a pressure of about 500 psi, and the Cold Box temperatures were simulated to operate at a temperature of about –105° C. The $C_2/C_2=$losses reported below do not include losses in the distillation train.

Comparative Example 1

FIG. 3 shows a typical ethylene plant which employs PSA. Briefly, the plant comprises a cracking section where fresh feedstock, a recycle stream, and steam are mixed and reacted at near atmospheric pressure and high temperature in a cracking furnace. The effluent 1 of this section (commonly referred to as "cracked gases") is compressed in an effluent compressor and dried in one or more driers (not shown). The compressed effluent is then introduced into a cryogenic section (Cold Box) where its temperature is reduced to a level such that separation of the components in the effluent can be performed by distillation. The refrigeration balance of the Cold Box is provided by an ethylene refrigeration cycle for the warmer part of the Cold Box and by expanders for the colder part of the Cold Box. The off-gas 6 providing refrigeration duty to the expanders is a mixture of methane and hydrogen.

The chilled effluent is then passed to a demethanizer to yield an overhead stream 4 comprising methane and hydrogen, and a distillation feedstream 5 containing heavier Comparative Example 2

FIG. 4 shows a typical ethylene plant which employs separate PSA and membrane systems. The process scheme in FIG. 4 is the same as in FIG. 3 except that a membrane system has been inserted after the feed compressor. A low pressure off-gas stream 3 comprising mainly hydrogen is rejected in the permeate stream to unload the Cold Box and the distillation section. The retentate stream 2 is processed in the same manner as the compressed cracking effluent described above.

The simulated results of the process scheme depicted in FIG. 4 are summarized in Table 2 below.

TABLE 2

| Membrane Recovery | 40% |
| L/V | 80% |
| PSA Recovery | 84% |
| $C_2/C_2=$ Loss | 2.8% |

| Stream No. | Cracker Outlet 1 | Permeate Stream 3 | Separator Feed 2 | Gas from Separator 4 | Expander Feed 6 | PSA Feed 7 | $H_2$ from PSA 8 | PSA Tail Gas 9 | To Distillation 5 |
|---|---|---|---|---|---|---|---|---|---|
| $H_2$ | 2500.0 | 1000.0 | 1500.0 | 1387.0 | 480.0 | 907.0 | 761.9 | 145.1 | 113.0 |
| $C_1$ | 2000.0 | 46.0 | 1954.0 | 346.8 | 108.0 | 238.8 | 0.0 | 238.8 | 1607.2 |
| $C_2=$ | 2700.0 | 54.0 | 2646.0 | 28.3 | 9.6 | 18.7 | 0.0 | 18.7 | 2617.7 |
| $C_2$ | 1300.0 | 22.1 | 1277.9 | 7.1 | 2.4 | 4.7 | 0.0 | 4.7 | 1270.8 |
| $C_3=$ | 1100.0 | 16.5 | 1083.5 | 0.0 | 0.0 | 0.0 | 0.0 | 0.0 | 1083.5 |
| $C_3$ | 400.0 | 15.6 | 384.4 | 0.0 | 0.0 | 0.0 | 0.0 | 0.0 | 384.4 |
| Total | 10000.0 | 1154.2 | 8845.8 | 1769.2 | 600.0 | 1169.2 | 761.9 | 407.3 | 7076.6 |
| $H_2$ (%) | 25.0 | 86.6 | 17.0 | 78.4 | 78.4 | 77.6 | 100.0 | 35.6 | 1.6 |
| $C_1$ (%) | 20.0 | 4.0 | 22.1 | 19.6 | 19.6 | 20.4 | 0.0 | 58.6 | 22.7 |
| $C_2=$ (%) | 27.0 | 4.7 | 29.9 | 1.6 | 1.6 | 1.6 | 0.0 | 4.6 | 37.0 |
| $C_2$ (%) | 13.0 | 1.9 | 14.4 | 0.4 | 0.4 | 0.4 | 0.0 | 1.1 | 18.0 |
| $C_3=$ (%) | 11.0 | 1.4 | 12.2 | 0.0 | 0.0 | 0.0 | 0.0 | 0.0 | 15.3 |
| $C_3$ (%) | 4.0 | 1.4 | 4.3 | 0.0 | 0.0 | 0.0 | 0.0 | 0.0 | 5.4 |
| Total (%) | 100.0 | 100.0 | 100.0 | 100.0 | 100.0 | 100.0 | 100.0 | 100.0 | 100.0 |

Example 1

FIG. 5 depicts an ethylene plant in accordance with the present invention. It advantageously employs a combination of PSA and membrane systems. Like in FIG. 4, the compressed effluent 10 is passed to a membrane separator. Unlike the scheme in FIG. 4, the permeate stream 3 is recompressed in an additional compressor and introduced as a feed into the PSA system. The tail gas 9 from the PSA system, which now contains valuable products present in the permeate stream 3, is sent to the suction side of the feed compressor and fed back to the distillation section. Pure hydrogen is recovered as the nonadsorbed stream 8 from the PSA system.

The simulated results of the process scheme depicted in FIG. 5 are summarized in Table 3 below.

By comparing the results of Example 1 with Comparative Examples 1 and 2, it can be seen that process according to the present invention can reduce the $C_2/C_2=$product losses to less than 0.5%.

While the invention has been described with reference to the figures, examples, and the preferred embodiments, it is to be understood that variations and modifications may be resorted to as will be apparent to those skilled in the art. Such variations and modifications are to be considered within the purview and the scope of the claims appended hereto.

What is claimed is:

1. A process for recovering olefins from a cracking effluent containing olefins and hydrogen, said process comprising the steps of:

TABLE 3

| Membrane Recovery | 40% |
| L/V | 78% |
| PSA Recovery | 84% |
| $C_2/C_2=$ Loss | 0.3% |

| Stream No. | Cracker Outlet 1 | Membrane Feed 10 | Permeate Stream 3 | Separator Feed 2 | Gas from Separator 4 | Expander Feed 6 | PSA Feed 7 | $H_2$ from PSA 8 | PSA Tail Gas 9 | To Distillation 5 |
|---|---|---|---|---|---|---|---|---|---|---|
| $H_2$ | 2500.0 | 2677.5 | 1071.0 | 1606.5 | 1571.5 | 462.0 | 1109.5 | 932.0 | 177.5 | 35.0 |
| $C_1$ | 2000.0 | 2302.6 | 48.1 | 2254.5 | 428.6 | 126.0 | 302.6 | 0.0 | 302.6 | 1825.9 |
| $C_2=$ | 2700.0 | 2723.1 | 56.4 | 2666.7 | 32.7 | 9.6 | 23.1 | 0.0 | 23.1 | 2634.0 |
| $C_2$ | 1300.0 | 1305.8 | 23.1 | 1282.7 | 8.2 | 2.4 | 5.8 | 0.0 | 5.8 | 1274.5 |
| $C_3=$ | 1100.0 | 1100.0 | 17.2 | 1082.8 | 0.0 | 0.0 | 0.0 | 0.0 | 0.0 | 1082.8 |
| $C_3$ | 400.0 | 400.0 | 16.3 | 383.7 | 0.0 | 0.0 | 0.0 | 0.0 | 0.0 | 383.7 |
| Total | 10000.0 | 10509.0 | 1232.1 | 9276.9 | 2040.9 | 600.0 | 1440.9 | 932.0 | 506.9 | 7236.0 |
| $H_2$ (%) | 25.0 | 25.5 | 86.9 | 17.3 | 77.0 | 77.0 | 77.0 | 100.0 | 34.9 | 0.5 |
| $C_1$ (%) | 20.0 | 21.9 | 3.9 | 24.3 | 21.0 | 21.0 | 21.0 | 0.0 | 59.5 | 25.2 |
| $C_2=$ (%) | 27.0 | 25.9 | 4.6 | 28.7 | 1.6 | 1.6 | 1.6 | 0.0 | 4.5 | 36.4 |
| $C_2$ (%) | 13.0 | 12.4 | 1.9 | 13.8 | 0.4 | 0.4 | 0.4 | 0.0 | 1.1 | 17.6 |
| $C_3=$ (%) | 11.0 | 10.5 | 1.4 | 11.7 | 0.0 | 0.0 | 0.0 | 0.0 | 0.0 | 15.0 |
| $C_3$ (%) | 4.0 | 3.8 | 1.3 | 4.1 | 0.0 | 0.0 | 0.0 | 0.0 | 0.0 | 5.3 |
| Total (%) | 100.0 | 100.0 | 100.0 | 100.0 | 100.0 | 100.0 | 100.0 | 100.0 | 100.0 | 100.0 |

(a) compressing said cracking effluent in at least one compression stage to form a compressed cracking effluent;

(b) contacting said compressed cracking effluent with a membrane at conditions effective to obtain a permeate stream rich in hydrogen and a retentate stream depleted in hydrogen; and (c) introducing said permeate stream into a pressure swing adsorption system at conditions effective to obtain a nonadsorbed stream rich in hydrogen and a desorbed stream comprising olefins.

2. The process according to claim 1, further comprising recycling at least a portion of said desorbed stream to said at least one compression stage.

3. The process according to claim 1, further comprising passing at least a portion of said desorbed stream to at least one additional compression stage to form a compressed desorbed stream and recycling at least a portion of said compressed desorbed stream to said membrane contacting step.

4. The process according to claim 1, wherein said olefins comprise ethylene.

5. The process according to claim 1, wherein said nonadsorbed stream comprises substantially pure hydrogen.

6. The process according to claim 1, further comprising passing said retentate stream to a cryogenic separation section.

7. The process according to claim 6, wherein said cryogenic separation section comprises a demethanizer having an overhead stream comprising methane and a bottoms stream comprising said olefins.

8. The process according to claim 7, further comprising recycling at least a portion of said overhead stream to said pressure swing adsorption system.

9. A process for recovering olefins and high purity hydrogen from a cracking effluent, said process comprising the steps of:

(a) compressing said cracking effluent in at least one compression stage to form a compressed cracking effluent;

(b) contacting said compressed cracking effluent with a membrane at conditions effective to obtain a permeate stream rich in hydrogen and a retentate stream depleted in hydrogen;

(c) compressing said permeate stream in at least one additional compression stage to form a compressed permeate stream;

(d) introducing said compressed permeate stream into a pressure swing adsorption system at conditions effective to obtain a nonadsorbed stream comprising high purity hydrogen and a desorbed stream comprising olefins; and (e) recycling said desorbed stream to said at least one compression stage.

10. The process according to claim 9, wherein said olefins comprise ethylene.

11. The process according to claim 9, further comprising passing said retentate stream to a cryogenic separation section.

12. The process according to claim 11, wherein said cryogenic separation section comprises a demethanizer having an overhead stream comprising methane and a bottoms stream comprising said olefins.

13. The process according to claim 12, further comprising contacting said overhead stream with a second membrane at conditions effective to obtain a permeate stream enriched in hydrogen and a retentate stream depleted in hydrogen.

14. The process according to claim 13, further comprising recycling at least a portion of said permeate stream to said pressure swing adsorption system.

* * * * *